United States Patent
Gerep

(10) Patent No.: US 7,337,655 B2
(45) Date of Patent: Mar. 4, 2008

(54) STUDDED BOILER TUBE WALL AND METHOD OF MEASURING CORROSION THEREON

(75) Inventor: Marcio Gerep, Chattanooga, TN (US)

(73) Assignee: Sage of America, inc., Ooltewah, TN (US)

( * ) Notice: Subject to any disclaimer, the term of this patent is extended or adjusted under 35 U.S.C. 154(b) by 65 days.

(21) Appl. No.: 10/729,815

(22) Filed: Dec. 5, 2003

(65) Prior Publication Data
US 2005/0120780 A1    Jun. 9, 2005

(51) Int. Cl.
*G01N 17/00* (2006.01)
(52) U.S. Cl. .......................................... 73/86
(58) Field of Classification Search .................... 73/86, 73/597, 598; 122/6 A, 6 R, 235.12; 165/134.1, 165/171, 181
See application file for complete search history.

(56) References Cited
U.S. PATENT DOCUMENTS

| | | |
|---|---|---|
| 2,077,410 A | 4/1937 | Harter et al. |
| 2,239,662 A | 4/1941 | Bailey |
| 3,139,866 A | 7/1964 | Lumm et al. |
| 3,476,180 A | 11/1969 | Straight, Jr. et al. |
| 4,019,445 A | 4/1977 | Stoia et al. |
| 4,423,513 A | 12/1983 | De Long |
| 4,669,310 A | 6/1987 | Lester |
| 4,685,334 A | 8/1987 | Latimer |
| 5,107,798 A | 4/1992 | Gerep |

*Primary Examiner*—Robert Raevis
(74) *Attorney, Agent, or Firm*—Buchanan Ingersoll & Rooney PC

(57) ABSTRACT

A studded wall in, or replacement panel for, a boiler or furnace has a plurality of substantially parallel tubes, each pair of adjacent tubes being connected. Separate regions of studs are attached to the wall. In each region every pair of adjacent studs is a selected distance apart, typically from one-eighth to one-half inch. The regions are configured and positioned to define a line between the regions. That line has a width different from the selected distance between the studs in the regions adjacent the line. Corrosion testing is done at selected points on the lines. The lines enable each successive test to be performed at the same locations.

31 Claims, 3 Drawing Sheets

STUDDED BOILER TUBE WALL AND METHOD OF MEASURING CORROSION THEREON

FIELD OF THE INVENTION

The present invention relates generally to boilers, such as pulp mill recovery boilers having walls formed of interconnected water-carrying heat-exchange tubes having studs welded to those tubes.

BACKGROUND OF THE INVENTION

In a pulp mill where paper is made, wood chips processed from debarked logs are cooked in a soda solution in a high-pressure vessel known as a digester. The soda solution at high temperature and pressure dissolves resins (lignin) binding cellulose fibers in the wood chips. The cellulose fibers are separated, washed, bleached and further processed to manufacture paper, or for other applications. After cellulose fiber separation, what is left is an aqueous solution. The aqueous solution is concentrated by evaporation to a concentration of approximately one-third water. The rest is combustible resin (lignin) and chemicals, which can be recovered. Up to 98% of the chemicals used in the process can be recovered. Moreover, the resins constitute an excellent fuel. Universal practice is to thus concentrate the solution by evaporation and make various chemical adjustments to form what is known as black liquor, and then to burn the black liquor as fuel in a recovery boiler.

A recovery boiler is a large structure; perhaps fifteen stories high, and thirty to forty feet (9.1 to 12.2 meters) wide. The lower portion of a recovery boiler where combustion occurs is known as the furnace, and is the hottest part. The walls of a recovery boiler are walls formed of water-carrying tubes that are heated by the combustion process to usefully generate steam. Within the recovery boiler, the resins constituting part of the black liquor are burned to produce heat and waste gases. Chemicals in the black liquor, such as soda, form a molten residue known as smelt, which is recovered. A complicating factor in this process is that the smelt temperature is approximately 2000° F. (1093° C.) to 2100° F. (1149° C.). The smelt and gases within the recovery boiler are chemically highly active at these temperatures. Also, during boiler operation, the black liquor is typically sprayed from a number of nozzles directly against the walls of the lower portion of the boiler. Thus, the carbon steel water-carrying tubes are subject to corrosion and eventual destruction, which necessitates replacement of the boiler wall. Moreover, failure of the water-carrying tubes is potentially catastrophic as an explosion can occur if water within the tubes comes into with the hot smelt which can be around, and sometimes is above, 2000° F.

A common practice in recovery boilers, particularly in the furnace portion, is to employ a multiplicity of cylindrical studs, analogous to heat-exchange fins, for corrosion protection. Each stud has a base or attachment end welded to the external surface of a water-carrying tube, and an exposed or tip end projecting radially outward from the tube. Conventional studs are made of low carbon steel and, when new, are typically ⅜ inch (0.95 cm) or ½ inch (1.27 cm) in diameter, and ¾ inch (1.91 cm) in length. The stud may have a sleeve of a different material as disclosed in my U.S. Pat. No. 5,107,798. Studs typically are applied at a uniform density of sixty or ninety studs per lineal foot (30.5 cm) of 2½ to 3-inch (6.5 to 7.62 cm) diameter water-carrying tube. The distance between adjacent rows of studs is called pitch while the distance between adjacent studs within a row is called spacing. A common pitch in the industry is one-fourth inch measured from the centers of the studs. Pitch is often somewhat larger than spacing, typically five-eights of an inch, but could be the same distance as the spacing. A recovery boiler may have anywhere from 100,000 to 1,000,000 studs in total.

It is standard practice in the industry to periodically measure the thickness of the walls of the tubes so that replacement can be made before the walls have corroded to such an extend that they rupture. Measurements are made with an ultrasonic probe using techniques similar to those described in U.S. Pat. Nos. 4,685,334 to Latimer and U.S. Pat. No. 4,669,310 to Lester. Before any measurements are made, the slag that has built up on the wall is removed. Since the slag in a pulp boiler is water soluble, simple washing removes the slag. Next, the portion of the tube to be tested is blasted to remove the oxide coating. Then a conductive gel is applied to the test location and the probe is placed against the gel on the wall of the tube. Ultrasonic waves are directed from the probe through the conductive gel into the tube wall and reflected waves are detected. The response time of the reflected waves is then used to calculate the thickness of the tube wall. The face of a typical probe used for such tests is one half inch or about one centimeter in diameter. Smaller diameter probes of about one-fourth inch in diameter could be used, but they tend to lose contact with the surface more easily than the half-inch diameter probes. Consequently, the larger, half-inch diameter probes are preferred. Several locations on the furnace wall are tested in a single test session.

Those who conduct these periodic tests strive to take their measurements at the same locations on the boiler wall for each successive test. Since the tubes and studs are subject to corrosion and erosion it is not possible to mark the location of a measurement made at one point in time and to have that mark be present when the next measurement is taken several weeks or months later. Consequently, the technicians conducting the tests take measurements from the base of the boiler wall or other reference point when the first test is conducted and try to use those measurements to find the same location when subsequent tests are made. The measurement process is time consuming and subject to error.

Repeated test measurements taken at the same location over time can be used to calculate a rate of corrosion. Knowing the corrosion rate enables the boiler operator to predict when tube failure will occur. Then the tube can be replaced before it fails. Most, if not all, boilers are shut down periodically for inspection and maintenance. The shutdowns are scheduled months in advance so as to have a minimum impact on the operation of the plant. Thus, the best time to replace a boiler tube is during a scheduled shutdown. But, the boiler owner does not want to replace tubes until they are close to the end of their useful life. The calculation of corrosion rates based upon repeated tests rests upon the assumption that successive measurements are taken at the same location. If measurements are taken in different locations they may lead to an erroneously determined corrosion rate. Yet, under the current practice, successive corrosion measurements are seldom made at precisely the same location.

There is a need for a studded boiler wall that is configured to enable easy corrosion testing while assuring that successive measurements are taken in precisely the same location.

SUMMARY OF THE INVENTION

I provide a studded wall in, or studded replacement panel for, a boiler or furnace. The wall or panel has a plurality of substantially parallel tubes. Adjacent tubes can be welded together directly, or be connected by a web. A set of first studs is attached to at least one tube and covers a first region located between the base and the top of the wall. Every pair of adjacent first studs along a row or column of studs is a first selected distance apart, typically from one-eighth to one-half inch. A set of second studs is attached to the same tube or tubes and covers a second region located between the base and the top of the wall. Every pair of adjacent second studs is a second selected distance from one another. That second distance may be the same as the first distance in the first region of studs. The first region and second region are configured and positioned to define a line between the regions. That line has a width different from the first selected distance and the second selected distance and is not less than one half inch. I prefer to provide several such regions separated by lines that together with the tubes form a grid pattern.

After the boiler has been operated for a selected period of time at least a portion of the wall is cleaned to remove any slag. Typically, the entire wall will be cleaned. If less than the entire wall is cleaned there must be a cleaned portion encompassing at least a portion of one line between the stud regions. A technician places an ultrasonic probe on the line at a point within the cleaned portion and measures a wall thickness of the tube at that point. The technician records the location of the point and the wall thickness for that recorded location. At some later time the test process is repeated to measure the wall thickness of the tube at the same point. The stud pattern enables the technician to return to the same point where the tube wall had been tested earlier. By comparing the first wall thickness measurement with a later wall thickness measurement a corrosion rate is determined. The process can be repeated each time the boiler is shut down for routine maintenance to create a corrosion profile for the boiler at selected locations where measurements have been taken.

DETAILED DESCRIPTION OF THE PREFERRED EMBODIMENTS

Figure 1:
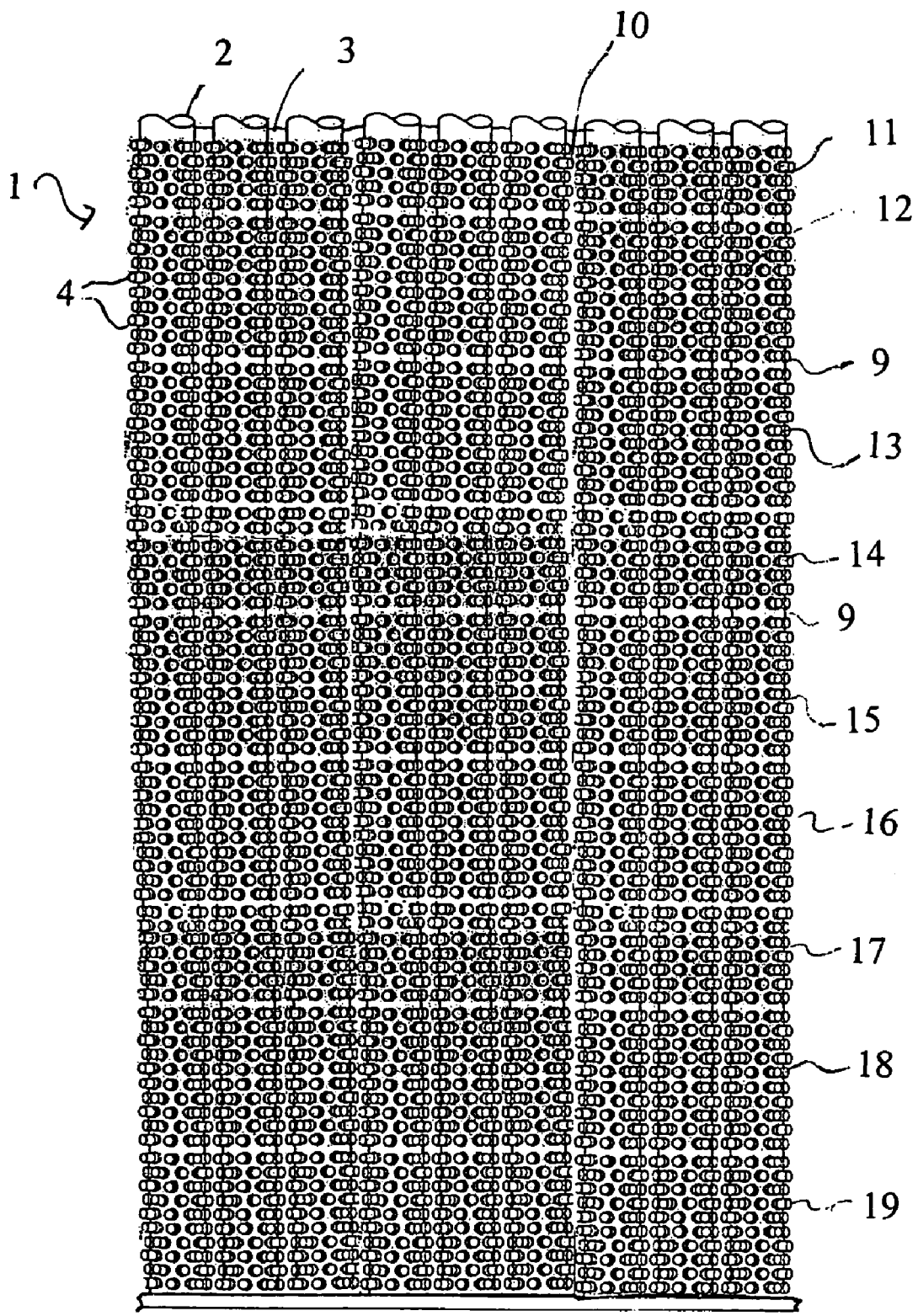
FIG. 1 is a front view of a portion of a present preferred studded boiler wall in accordance with the present invention.
Figure 2:
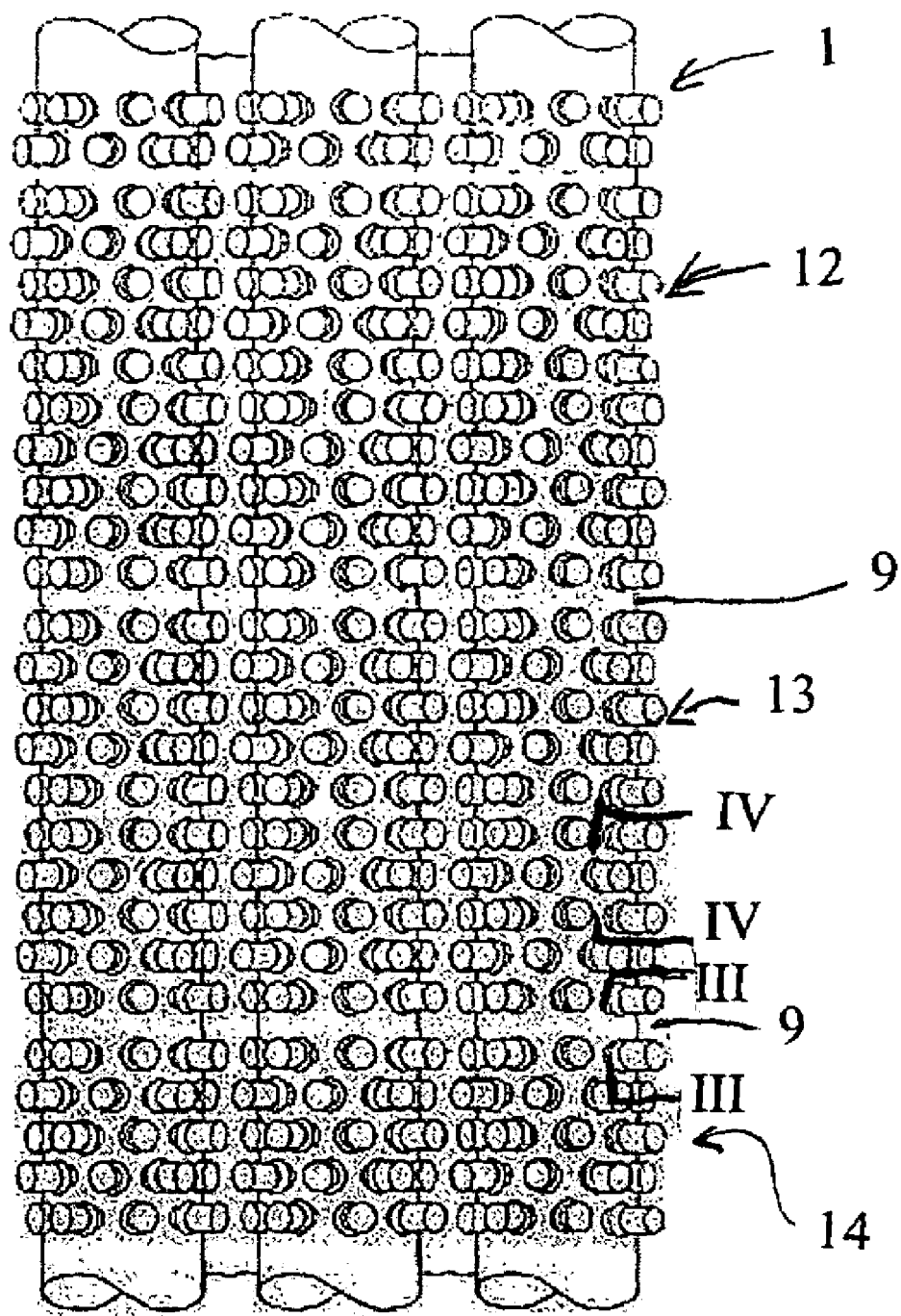
FIG. 2 is fragmentary view of a portion of the boiler wall shown in FIG. 1.

A present preferred embodiment of a boiler wall 1 made in accordance with the present invention has a series of parallel water carrying tubes 2 with adjacent tubes being connected by a web 3 as shown in FIGS. 1 and 2. Alternatively the tubes 2 could be directly connected together without webs between adjacent tubes. In a typical recovery boiler the tubes will have a diameter of about three inches. Studs 4 are applied to the portion of the tubes that faces the combustion chamber of the boiler. In the embodiment here illustrated rows of studs are applied to each tube such that one row of studs is offset from the adjacent row of studs. Consequently, a vertical line through any stud will not pass through a stud in an adjacent row, but will pass through studs on every second row. The studs 4, seen more clearly in FIGS. 3 and 4, have a cylindrical body 6 and a collar 5. Studs of different geometrics could be used. The studs are preferably made of low carbon steel and may have a sleeve of a different material as disclosed in my U.S. Pat. No. 5,107,778. When new, each stud is typically ⅜ inch (0.95 cm) or ½ inch (1.27 cm) in diameter, and ¾ inch (1.91 cm) in length. Studs could be from 10 to 12 mm in diameter. The collar is about ⅛ inch (0.32 cm) wide.

I provide a studded wall in a boiler or furnace, where the high density of studs is high enough to make the insertion of a probe in between studs either impossible or cumbersome. To enjoy the benefits of higher density of studs without jeopardizing the ultrasonic inspection the studs will be applied in such a manner that at every linear foot along the tube a larger pitch is used to enable the insertion of the probe. A common pitch in the industry is ¼". So I prefer to provide two or more consecutive lines with a pitch of ¼" of an inch. For the next line I provide a pitch of more than ¼ of an inch, typically ⅝". This spacing provides higher density, therefore, better cooling, better protection, therefore longer life for the panel, and still the ability to monitory the wall thickness of the tubes. One looking at a wall made in this way would see distinct bands of studs 11 through 19 separated by lines 9 defined by the larger pitch separating studs adjacent regions.

In another preferred embodiment there are 90 studs per lineal foot of tube and the spacing between adjacent studs in any row or column of studs is about one half inch at the top of the stud and about ⅛ inch at the collars. The studs are applied in regions or bands 11 through 19 of about six or twelve inches in height. In yet another preferred embodiment a row of studs is periodically omitted from the stud pattern to create a horizontal line 9 between each pair of adjacent regions of studs. In all embodiments the pitch between studs on either side of the line 9 is greater than the pitch between adjacent studs within each region. The width of the line 9 must accommodate an ultrasonic probe and preferably is at least one-half inch wide. This width is sufficiently different from the spacing of studs within each region to be noticeable by a technician entering the boiler to conduct corrosion tests on the tubes. In a present preferred embodiment, the width of line 9 is ⅝ (0.625) inches while the spacing of adjacent studs from center to center is ¼ (0.25) inches. Although not preferred, the spacing of line 9 could be less than the spacing between adjacent studs within a region and still define a noticeable line. In the boiler wall shown in FIG. 1, the regions 11 through 19 are separated by horizontal lines 9 having a width greater than the distance between adjacent studs within the region. Lines 9 are sufficiently wide to permit a probe to fit easily against the tube wall at any point along each line. It is possible to define regions by vertical lines similar to lines 9. But, for most applications vertical lines should be avoided because a vertical line without studs may allow liquid smelt to freely run down the furnace wall and corrode the tube. Diagonal lines may also be used. However, if the slope of the diagonal lines is steep, liquid smelt could freely run down the furnace wall along the diagonal line corroding the tubes. Therefore, steep diagonal lines are not recommended.

Figure 3:
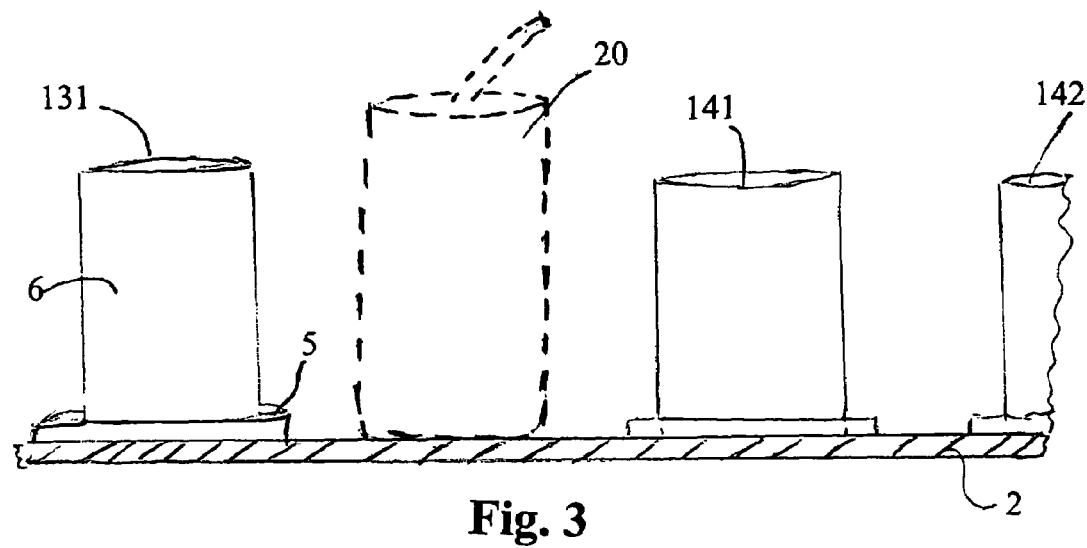
FIG. 3 is sectional view taken along the line III-III of FIG. 2 with a corrosion probe, shown in dotted line, positioned on the tube wall.
Figure 4:
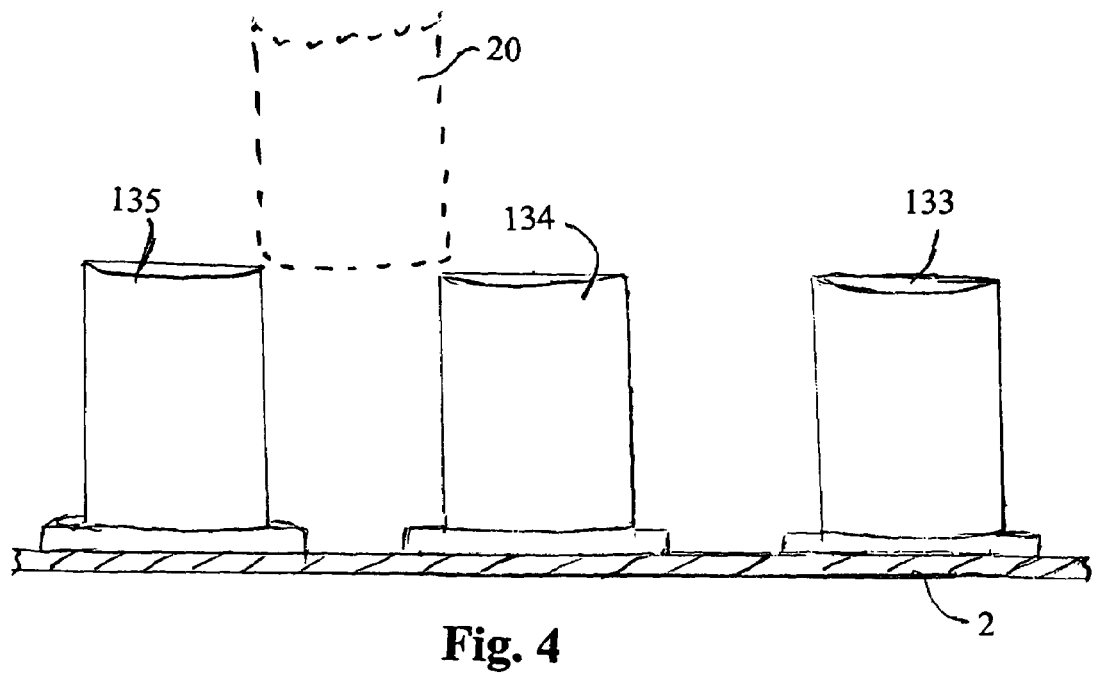
FIG. 4 is sectional view taken along the line IV-IV of FIG. 2 wherein the stud configuration of this section prevents the corrosion probe, shown in dotted line, from being positioned on the tube wall.

Turning to FIGS. 2, 3 and 4, stud 131 from region 13 is at a greater distance from stud 141 in region 14 than the spacing between adjacent studs within each region. As can be seen in FIGS. 3 and 4 the distance between studs 141 and 142, between studs 135 and 134 and between studs 134 and 133 is less than the distance between studs 131 and 141. Indeed, the distances are selected so that an ultrasonic probe 20 will fit between studs 131 and 141 that are in different, but adjacent regions. But, the probe 20 will not fit between adjacent studs in a single region, such as stud 134 and stud 135 or stud 134 and stud 133. Consequently, the only place that corrosion tests can be made is within lines 9. Since lines 9 and tubes 2 form a grid pattern it is easy for a corrosion test technician to record where each corrosion reading is taken in the first test session and than precisely find those points for each successive test. In all of the preferred embodiments the lack of consistency in pitch creates one or more noticeable lines along which corrosion measurements are made. Taking readings at locations other than along a line is either impossible because the probe will not fit or visibly cumbersome and not intuitive.

Although the entire length of the furnace wall is covered with studs in the preferred embodiment, this is not necessary to practice the present invention. There must only be sufficient studs applied in a manner to define two or more regions of studs positioned to define a line between adjacent regions. That line would indicate where corrosion testing is to be done.

In the present preferred embodiment the studs within each region are placed so close to one another so as to prevent a probe from being placed on the tube between any adjacent studs within the region. Such spacing is preferred, but not required. Rather the spacing of adjacent regions must simply be different from the spacing between studs along a line between adjacent regions. Furthermore, the difference in spacing must be such to define a noticeable line between adjacent regions. In the preferred embodiment the studs within each region are closer together than those along a line between two regions. However, the spacing between studs within a region could be greater than the spacing of studs along a line between adjacent regions so long as the width of the line is large enough to accept a probe.

In the present preferred embodiment the spacing between adjacent studs in one region is the same as the spacing between adjacent studs in all the other regions. However, this is not necessary as the spacing could differ from region to region. Nevertheless, the spacing must define a line between regions.

A boiler having a wall as disclosed in the drawings is tested periodically in this way. When the boiler is installed the thickness of the walls of all tubes is known and preferably is the same. After some period of operation the boiler is shut down and cleaned. The technician selects points on the boiler wall along lines 9. Those points are blasted to remove oxide, a conductive gel is applied and ultrasonic measurements are taken. Those measurements are converted into wall thickness. Each point is recorded according to coordinates based upon a grid formed by lines 9 and the tubes. Then, the wall thickness for each point is recorded. The boiler is placed back in operation and tested again in the same manner several weeks or months later. For each successive test the technician refers to the grid lines and recorded coordinates of each measurement point to assure that all successive tests are conducted at the same location. Then the difference in wall thickness from successive measurements is used to calculate corrosion rates at each measurement point. This information enables the boiler owner to replace the tubes during scheduled shut downs and before the tube walls become so thin that they can rupture.

If desired, the successive measurements could be plotted over time to provide a visual display of corrosion that has occurred in the boiler or furnace being tested. The data may also be used in an algorithm that creates other types of visual displays or predicts when the tube will fail or when the tube will have corroded to a selected thickness. Such displays and other output may individually or collectively be considered as a corrosion profile for the boiler or furnace.

It is quite common in the industry to replace portions of a furnace wall rather than the entire wall. Indeed, boiler owners often purchase and install replacement panels. I also provide studded replacement panels in which there are two or more regions of studs with the pitch being the same within a region but different between regions. Preferably, the pitch between regions is greater than the pitch within a region. The studded replacement panels would look like a segment of the furnace wall described and illustrated in FIGS. 1 through 4.

While I have described the present invention in the content of recovery boilers used in the pulp and paper industry, the invention is not limited to such structures. Rather, the present invention can be used in all types of boilers and furnaces that have walls of water filled tubes. For example, some waste incinerators have studded tube walls. It should also be understood that the invention is not limited to the preferred embodiments here disclosed but may be variously embodied within the scope of the following claims.

I claim:

1. A studded wall for use in a boiler or furnace comprising:
   a plurality of substantially parallel tubes, each pair of adjacent tubes connected together to form a wall having a base and a top;
   a set of first studs attached to at least one tube and covering a first region located between the base and the top of the wall such that any pair of adjacent first studs is a first selected distance apart; and
   a set of second studs attached to the at least one tube and covering a second region located between the base and the top of the wall such that any pair of adjacent second studs is a second selected distance from one another;
   wherein the first region and second region are configured and positioned to define a line between the regions, the line having a width different from the first selected distance and the second selected distance and there being no studs on the line; and
   wherein the width of the line is greater than the first selected distance and greater than the second selected distance.

2. The studded wall of claim 1 wherein the width of the line is at least one-half inch.

3. The studded wall of claim 1 wherein the first selected distance and the second selected distance are equal.

4. The studded wall of claim 1 wherein the first studs and the second studs are cylindrical.

5. The studded wall of claim 4 wherein the first studs and the second studs each further comprises a collar.

6. The studded wall of claim 1 wherein at least one of the first selected distance and the second selected distance is 0.25 inches.

7. The studded wall of claim 1 also comprising a set of third studs attached to the at least one tube and covering a third region located between the base and the top of the wall such that any pair of adjacent third studs is a selected third distance from one another, wherein the third region is configured and positioned to define a second line between the second region and the third region, the second line having a width different from the second selected distance and the third selected distance, the line being a second selected elevation above the base of the wall and there being no studs on the second line.

8. The studded wall of claim 7 wherein the width of the second line is at least one-half inch.

9. The studded wall of claim 7 wherein the first selected distance, the second selected distance and the third selected distance are equal.

10. The studded wall of claim 1 wherein the first studs and the second studs have a diameter of from 10 mm to 12 mm.

11. The studded wall of claim 1 wherein the studs have a height of at least ¾ inch.

12. The studded wall panel of claim 1 wherein the wall formed by the connected tubes is a replacement panel for a boiler.

13. An improved studded replacement panel for use in a boiler or furnace of the type having a plurality of adjacent rows of studs attached to a plurality of connected tubes wherein the improvement comprises the studs being grouped into at least two sets such that spacing between adjacent rows of studs within a set is different from spacing between adjacent rows of studs from different sets.

14. The improved studded replacement panel of claim 13 wherein rows of studs within a set are positioned so that an ultrasonic probe cannot fit between adjacent rows of studs within a set.

15. The improved studded replacement panel of claim 13 wherein adjacent rows of studs within a set are not more than 0.25 inches apart.

16. The improved studded replacement panel of claim 13 wherein adjacent rows of studs from different sets are at least one-half inch apart.

17. An improved boiler or furnace of the type having at least one wall containing a replaceable panel of the type having a plurality of rows of studs attached to a plurality of connected tubes wherein the improvement comprises the studs being grouped into at least two sets such that spacing between adjacent rows of studs within a set is different from spacing between adjacent rows of studs from different sets.

18. The improved boiler or furnace of claim 17 wherein rows of studs within a set are positioned so that an ultrasonic probe cannot fit between adjacent rows of studs within a set.

19. The improved boiler or furnace of claim 17 wherein adjacent rows of studs within a set are not more than 0.25 inches apart.

20. The improved boiler or furnace of claim 17 wherein adjacent rows of studs from different sets are at least one-half inch apart.

21. An improved boiler of the type having at least one studded boiler wall having a base, a top, and comprised of a plurality of substantially parallel tubes, each pair of adjacent tubes connected together wherein the improvement comprises the at least one studded boiler wall comprising:
    a set of first studs attached to at least one tube and covering a first region located between the base and the top of the wall such that any pair of adjacent first studs is a first selected distance apart; and
    a set of second studs attached to the at least one tube and covering a second region located between the base and the top of the wall such that any pair of adjacent second studs is a second selected distance from one another;
    wherein the first region and second region are configured and positioned to define a line between the regions, the line having a width different from the first selected distance and the second selected distance and there being no studs on the and line; and
    wherein the width of the line is greater than the first selected distance and greater than the second selected distance.

22. The improved boiler of claim 21 wherein the width of the line is at least one-half inch.

23. The improved boiler of claim 21 wherein the first selected distance and the second selected distance are equal.

24. The improved boiler of claim 21 wherein the first studs and the second studs are cylindrical.

25. The improved boiler of claim 24 wherein the first studs and the second studs each further comprises a collar.

26. The improved boiler of claim 21 wherein at least one of the first selected distance and the second selected distance is 0.25 inches.

27. The improved boiler of claim 21 also comprising a set of third studs attached to the at least one tube and covering a third region located between the base and the top of the wall such that any pair of adjacent third studs is a selected third distance from one another, wherein the third region is configured and positioned to define a second line between the second region and the third region, the second line having a width different from the second selected distance and the third selected distance, the second line being a second selected elevation above the base of the wall and there being no studs on the second line.

28. The improved boiler of claim 27 wherein the width of the second line is at least one-half inch.

29. The improved boiler of claim 27 wherein the first selected distance, the second selected distance and the third selected distance are equal.

30. The improved boiler of claim 21 wherein the first studs and the second studs have a diameter of from ⅜ inches to ½ inch.

31. The improved boiler of claim 21 wherein the studs have a height of at least ¾ inch.

* * * * *